United States Patent
Boivin et al.

(10) Patent No.: US 7,250,108 B2
(45) Date of Patent: Jul. 31, 2007

(54) METHOD FOR MEASURING THE LOCAL HYDRAULIC PERMEABILITY OF A SUB-GROUP OF HOLLOW FIBRE OF A BUNDLE OF HOLLOW FIBRES

(75) Inventors: Didier Boivin, Caluire et Cuire (FR); Jean Farjaud, Meyzieu (FR)

(73) Assignee: Gambro Industries SAS, Meyzieu (FR)

(*) Notice: Subject to any disclaimer, the term of this patent is extended or adjusted under 35 U.S.C. 154(b) by 317 days.

(21) Appl. No.: 10/874,303
(22) Filed: Jun. 24, 2004

(65) Prior Publication Data

US 2004/0232062 A1    Nov. 25, 2004

Related U.S. Application Data

(62) Division of application No. 09/984,225, filed on Oct. 29, 2001, now Pat. No. 6,773,591.

(30) Foreign Application Priority Data

Oct. 30, 2000  (FR)  ................................. 00 13920

(51) Int. Cl.
*B01D 63/02* (2006.01)
*B01D 63/00* (2006.01)
(52) U.S. Cl. .............. 210/87; 210/321.88; 210/321.87; 210/321.89; 210/500.23
(58) Field of Classification Search ........... 210/321.89, 210/500.23, 500.41, 87, 88, 89, 650, 321.78, 210/321.79, 321.8, 321.88
See application file for complete search history.

(56) References Cited

U.S. PATENT DOCUMENTS 3,546,209 A    12/1970  Lapre, Jr. ................... 260/214

(Continued)

FOREIGN PATENT DOCUMENTS

EP    0 042 517    12/1981

(Continued)

OTHER PUBLICATIONS

"PC-PE Hollow Fiber Membrane," H. Gohl et al. Blood Purification 4: 23-31 (1986).

(Continued)

*Primary Examiner*—Krishnan S. Menon
(74) *Attorney, Agent, or Firm*—Finnegan, Henderson, Farabow, Garrett & Dunner, L.L.P.

(57) ABSTRACT

A method is provided for measuring the local hydraulic permeability, Lpi, of a sub-group of hollow fibres of a bundle of hollow fibres mounted in a tubular casing. The method comprises a step of placing the casing containing the bundle in a vertical position, the lateral opening of the casing being disposed toward the bottom, and sealing the lower end of the casing. A graduated, calibrated tube is applied in a vertical position over a portion of the upper cut surface of the bundle to form a sealed connection there between. A liquid is passed through the lateral opening of the casing at a defined flow rate, and the time required for the liquid to pass from a first graduation to a second graduation of the tube is measured. Lpi can then be calculated from the formula $Lpi=V/tPSi$ in which; V represents the volume of the tube between the two graduations; t represents the time that the liquid takes to pass from the first graduation to the second graduation of the tube; P represents the transmembrane pressure; and Si represents the surface area of the hollow fibres belonging to the sub-group under consideration for the measurement.

12 Claims, 9 Drawing Sheets

U.S. PATENT DOCUMENTS

| | | | |
|---|---|---|---|
| 3,773,534 A | 11/1973 | Kaiser et al. | 106/178 |
| 3,990,973 A | 11/1976 | Boag et al. | 210/87 |
| 4,354,938 A | 10/1982 | Walch et al. | 210/637 |
| 4,762,620 A * | 8/1988 | Sama | 210/646 |
| 4,888,115 A * | 12/1989 | Marinaccio et al. | 210/636 |
| 4,900,444 A | 2/1990 | Seita et al. | 210/500.36 |
| 4,906,375 A | 3/1990 | Heilmann | 210/500.23 |
| 4,935,141 A | 6/1990 | Buck et al. | 210/500.38 |
| 5,084,349 A | 1/1992 | Sasaki et al. | 428/398 |
| 5,192,440 A | 3/1993 | Von Sengbusch | 210/500.29 |
| 5,288,308 A * | 2/1994 | Puri et al. | 96/8 |
| 5,320,747 A * | 6/1994 | Ford et al. | 210/94 |
| 5,505,851 A | 4/1996 | Wagener et al. | 210/490 |
| 5,578,267 A | 11/1996 | Cosentino et al. | 422/46 |
| 5,693,694 A | 12/1997 | Chu et al. | 524/104 |
| 5,700,372 A | 12/1997 | Takesawa et al. | 210/321.81 |
| 5,736,046 A | 4/1998 | Althin et al. | 210/500.23 |
| 5,851,394 A | 12/1998 | Shibata et al. | 210/500.23 |
| 5,879,554 A | 3/1999 | Loffelmann et al. | 210/500.23 |
| 5,891,338 A | 4/1999 | Bell et al. | 210/500.32 |
| 5,897,817 A | 4/1999 | Radovich et al. | 264/41 |
| 5,919,370 A | 7/1999 | Röttger et al. | 210/646 |
| 6,019,925 A | 2/2000 | Diamantoglou et al. | 264/203 |
| 6,251,275 B1 | 6/2001 | Rekers | 210/321.78 |
| 6,258,321 B1 | 7/2001 | Van Driel et al. | 422/44 |

FOREIGN PATENT DOCUMENTS

| | | |
|---|---|---|
| EP | 0 232 442 | 8/1987 |
| EP | 0345 780 | 12/1989 |

OTHER PUBLICATIONS

Database WPI week 198015 Derwent Publication Ltd., London, GB; AN 1980-26293C XP002175653 1.

Nippon Zeon KK, "Liquid Blood Filtering Device Includes Hollow Fibre Yarns with Different Ultrafiltering Speeds Contained in Casing," Patent Abstracts of Japanese Publication No. JP 55-028728, Feb. 29, 1980.

Rapport De Recherche Préliminaire of French Patent Application No. FR 0109494; Feb. 19, 2002.

Rapport De Recherche Préliminaire of French Patent Application No. FR 0013920; Aug. 23, 2001.

Search Report of European Patent Application EP 01 20 4054; Feb. 19, 2002.

Document including English language Abstracts of DE 021943 of JP 053108; dated Apr. 15, 1982.

* cited by examiner

METHOD FOR MEASURING THE LOCAL HYDRAULIC PERMEABILITY OF A SUB-GROUP OF HOLLOW FIBRE OF A BUNDLE OF HOLLOW FIBRES

This application is a divisional of U.S. patent application Ser. No. 09/984,225, filed Oct. 29, 2001 now U.S. Pat. No. 6,777,591, which claims priority under 35 U.S.C. §119 to French Patent Application No. 00 13920, filed Oct. 30, 2000, both of which are incorporated herein by reference.

The present invention relates to a bundle of hollow fibres for a device for treating blood or plasma by extracorporeal circulation, and to a process for producing a bundle of hollow fibres constituting the semi-permeable membrane of the device.

Membrane devices for treating blood or plasma by extracorporeal circulation are used in many different medical or paramedical applications, such as treating renal insufficiency by dialysis or haemofiltration, plasmapheresis and apheresis for therapeutic and non-therapeutic purposes, oxygenating blood, immunopurification, etc.

In general, semi-permeable membranes can be classified by their hydraulic permeability into low flux membranes, medium flux membranes and high flux membranes.

Hydraulic permeability describes the quantity of water that can be ultrafiltered through a semi-permeable membrane with a given active surface area, at a given transmembrane pressure over a given time period. Simultaneously with the water ultrafiltration, salts and toxins traverse the semi-permeable membrane. Eliminating the different solutes depends on a property of the membrane known as the rejection rate or transmittance (transmittance=1 or rejection rate=0 for solutes traversing the membrane with no change in concentration, rejection rate=100% and transmittance=0 for completely cleared solutes). The transmittance of a particular molecule is defined as the ratio of the concentration of the molecule in ultrafiltered water (ultrafiltrate) to its mean concentration in the unfiltered fraction of the blood.

With high flux semi-permeable membranes, i.e., with a hydraulic permeability of at least $31 \times 10^{-12}$ m$^3$/s.Pa.m$^2$ (15 ml/h.mmHg.m$^2$), the quantity of water extracted from the blood must be regulated using a water extraction controller. Devices provided with a high flux membrane run the risk of reverse filtration or back filtration, which consists of migration of a portion of the dialysis solution into the blood.

The dialysis solution, which has an electrolytic composition that is close to that of a normal extracellular liquid, is usually a non-sterile aqueous solution. Before use, the dialysis solution is normally free of solutes to be eliminated from the blood, but can contain foreign substances or pyrogenic substances, for example as a result of microbial contamination. Dialysis solution is not intended for injection into the blood and thus does not have the quality of an injectable liquid. With back filtration, then, there is then a risk of causing foreign or pyrogenic substances to enter the blood with the dialysis solution.

As is known, back filtration can be minimised by using semi-permeable low flux membranes with a hydraulic permeability of less than $12.5 \times 10^{-12}$ m$^3$/s.Pa.m$^2$ (6 ml/h.mmHg.m$^2$), or medium flux semi-permeable membranes with a permeability of between about 12.5 and about $31 \times 10^{-12}$ m$^3$/s.Pa.m$^2$ (between about 6 and about 15 ml/h.mmHg.m$^2$). However, the reduction in hydraulic permeability is generally accompanied by a reduction in transmittance, i.e., a reduction in the fraction of certain molecules that pass by convection through the pores of the membrane and which are intended to be eliminated from the blood.

Thus, one aim of the invention is to provide a device for treating blood or plasma by extracorporeal circulation, comprising a semi-permeable membrane with a reduced overall hydraulic permeability to limit the risks of reverse filtration, while retaining satisfactory transmittances, in particular those for toxins and proteins.

A further aim of the invention is to provide a device for treating blood or plasma by extracorporeal circulation comprising a semi-permeable membrane, the characteristics (hydraulic permeability, transmittances) of which can be adjusted independently of each other to a certain extent such that the hydraulic permeability of the membrane is low flux, medium flux or high flux, while the transmittances, in particular as regards toxins and proteins, are maintained at satisfactory values.

In a first aspect of the invention, these aims are achieved by a bundle of hollow fibres intended to constitute the semi-permeable membrane of a device for treating blood or plasma by extracorporeal circulation, in which:
  the distribution of the hollow fibres in the bundle is heterogeneous; and
  the internal diameter and wall thickness of the hollow fibres located in the zones most dense in hollow fibres are respectively greater than the internal diameter and wall thickness of the hollow fibres located in the least dense zones.

Preferably, the internal diameter and wall thickness of the hollow fibres located in the zones least dense in hollow fibres are respectively a minimum of 180 microns and 40 microns.

In a variation of the invention:
  the heterogeneity of the distribution of the hollow fibres in the bundle corresponds to a higher density of hollow fibres around at least a portion of the periphery of the bundle compared with a density of hollow fibres at the centre of the bundle; and
  the internal diameter and wall thickness of the hollow fibres located at the periphery of the bundle are respectively greater than the internal diameter and wall thickness of the hollow fibres located at the centre of the bundle.

In a second aspect of the present invention, the above aims are achieved by a bundle of hollow fibres intended to constitute the semi-permeable membrane of a device for treating blood or plasma by extracorporeal circulation, in which:
  the hydraulic permeability of the hollow fibres in the bundle is heterogeneous; and
  the ratio of the highest hydraulic permeability measured on some hollow fibres of the bundle to the lowest hydraulic permeability measured on other hollow fibres of the same bundle is at least about 5.

In a variation of the invention, the heterogeneity of the hydraulic permeability in the bundle corresponds to a higher hydraulic permeability around at least a portion of the periphery of the bundle compared with a hydraulic permeability of the bundle fibres, such that the ratio of the highest hydraulic permeability measured at the periphery of the bundle to the lowest hydraulic permeability measured at the centre of the bundle is at least about 5.

In a further variation of the invention, the heterogeneity of the hydraulic permeability is associated with a heterogeneity of the distribution of the hollow fibres in the bundle, the hydraulic permeability being higher in the zones most dense in hollow fibres and lower in the zones least dense in hollow fibres.

Advantageously, the internal diameter and wall thickness of the hollow fibres located in the zones most dense in hollow fibres are respectively greater than the internal diameter and wall thickness of the hollow fibres located in the zones least dense in hollow fibres. Advantageously again, the internal diameter and wall thickness of the hollow fibres located in the zones least dense in hollow fibres are respectively a minimum of 180 microns and 40 microns.

In one embodiment of the invention, the overall hydraulic permeability of the bundle of hollow fibres is in the range $10 \times 10^{-12}$ to $312 \times 10^{-12}$ m$^3$/s.Pa.m$^2$ (5 to 150 ml/h.mmHg.m$^2$), the lowest hydraulic permeability measured at the centre of the bundle is less than $17 \times 10^{-12}$ m$^3$/s.Pa.m$^2$ (8 ml/h.mmHg.m$^2$) and the highest hydraulic permeability measured at the periphery of the bundle is more than $42 \times 10^{-12}$ m$^3$/s.Pa.m$^2$ (20 ml/h.mmHg.m$^2$).

In a further embodiment, the overall hydraulic permeability of the bundle of hollow fibres is in the range $42 \times 10^{-12}$ to $146 \times 10^{-12}$ m$^3$/s.Pa.m$^2$ (20 to 70 ml/h.mmHg.m$^2$), the lowest hydraulic permeability measured at the centre of the bundle is less than $17 \times 10^{-12}$ m$^3$/s.Pa.m$^2$ (8 ml/h.mmHg.m$^2$), the highest hydraulic permeability measured at the periphery of the bundle is more than $83 \times 10^{-12}$ m$^3$/s.Pa.m$^2$ (40 ml/h.mmHg.m$^2$) and the ratio of the highest hydraulic permeability measured at the periphery of the bundle to the lowest hydraulic permeability measured at the centre of the bundle is at least 10.

Within the context of the present invention, the overall hydraulic permeability Lp of the bundle is conventionally obtained by measuring the filtration time t of a volume V of water at a mean transmembrane pressure P of the order of 50 to 500 mmHg through a surface area S of membrane at a given temperature (see European standard EN 12.83). The hydraulic permeability Lp is expressed in m$^3$/s.Pa.m$^2$ or ml/h.mmHg.m$^2$ and corresponds to formula (I):

$$Lp = V/(tPS) \quad (I)$$

To evaluate the heterogeneity of the hydraulic permeability of hollow fibres inside a bundle, within the context of the present invention a method has been developed for measuring the hydraulic permeability of a sub-group of hollow fibres of the bundle, the number of hollow fibres in the evaluated sub-group being substantially the same for each measurement. The hydraulic permeability of a sub-group of hollow fibres will be termed the "local hydraulic permeability Lpi" in the description. In general, the method for measuring the local hydraulic permeability Lpi of a sub-group of hollow fibres of a bundle of hollow fibres mounted in a tubular casing comprising a lateral opening at one of its ends, the bundle of hollow fibres being fixed in the casing by an adhesive seal at each of its ends, and the adhesive seals having been cut perpendicular to a longitudinal axis of the bundle to open the fibres, comprises steps discussed in further detail below. The conditions for this measurement are diagrammatically shown in the accompanying FIG. 1 and are described in detail below. The local hydraulic permeability Lpi measurements are preferably carried out on a ready-to-use hollow fibre device for the treatment of blood or plasma by extracorporeal circulation, i.e. after assembling the various components of the hollow fibre device, in particular by mounting bundle 1 of hollow fibres in a tubular casing 2 comprising, at each of its ends, a lateral opening 5 and 6 (inlet/outlet channels) and by setting seals 3 and 4, after having separated the hollow fibres from each other at their ends, for example by riffling or brushing their ends, manually or with a stream of air. This allows the ends of hollow fibres that have stuck together to be separated and eliminates the risk of leakage into the seal. As is well known, the sealing operation consists of securing the two ends of the bundle of hollow fibres by adhesive bonding using a seal in which a portion of the length of the fibres is embedded, the ends of the fibres being left open. Then the adhesive seals, in which the open ends of the hollow fibres are secured by adhesive and substantially uniformly distributed, are cut. To measure the local hydraulic permeability, casing 2 containing the bundle of hollow fibres is placed in a vertical position, and a seal is produced at the lower end of the casing (and as a result the lower cut surface of the bundle) by pressing it on a plate 11 to ensure a seal, for example a plate of flexible plastics material such as a silicone. A liquid, for example water or a dialysis liquid, is then passed at a flow rate of 80 ml/min, for example, through the lower lateral opening 6 while the upper lateral opening 5 is closed. A calibrated tube 12, in the vertical position, is applied to a portion of the upper cut surface of the bundle to measure the local flow rate at the upper end of the casing. To carry out the measurement, calibrated tube 12 is firmly applied against the portion of the upper cut surface to be evaluated (in the figure, against the centre of the bundle of hollow fibres), to form an intimate connection between the upper cut surface and the calibrated tube 12. A flow of liquid is applied via lower lateral opening 6 of casing 2 and the time t that the liquid takes to pass from a given first graduation 13 to a second given graduation 14 provided on calibrated tube 12 is measured. From the local measured flow rate (corresponding to the defined volume V of tube 12 between the two graduations 13,14 related to the time t for the liquid to pass from graduation 13 to graduation 14) and the known values of the transmembrane pressure P and the surface area Si of the hollow fibres in the sub-group on which the local flow rate is being measured, the local hydraulic permeability Lpi is measured using the following formula (II):

$$Lpi = V/(tPSi) \quad (II).$$

The dimensions of the calibrated tube 12 are not critical. They are suitable to allow local measurement of the flow rate. Thus the diameter of calibrated tube 12 can be 3.2 cm and its height can be of the order of 50 cm.

It should be noted that the local hydraulic permeability measured with the above method corresponds in fact to back filtration (passage of liquid from the dialysate compartment to the blood compartment, as conventionally defined, in particular via the insides of the hollow fibres), but other tests carried out by the Applicant have shown that the value of the hydraulic permeability of the hollow fibres does not depend on the direction of passage of the liquid.

By carrying out local hydraulic permeability measurements over the whole of the upper cut surface of the bundle of hollow fibres, the local hydraulic permeability can be mapped to show the variation with measurement zone. In this respect, it should be noted that the number of hollow fibres evaluated during each local hydraulic permeability measurement is substantially constant. The operation of separating the hollow fibres from each other at their ends prior to sealing homogenises the hollow fibre density at the ends of the bundle.

In accordance with the present invention, the devices for treating blood or plasma by extracorporeal circulation contain a bundle composed of an assembly of hollow fibres that differ from each other by their hydraulic permeability, certain hollow fibres being low flux while other hollow fibres are high flux. Overall, devices according to the present invention have the advantage of being capable of being high flux, medium flux or low flux depending on the local hydraulic permeabilities of the hollow fibres in the bundle.

The devices of the invention have the further advantage of having higher transmittance values than those obtained with conventional devices with an equivalent hydraulic permeability.

Thus, in the present invention, the devices can have a transmittance for cytochrome C of about 0.1 to about 0.6 (measured under the conditions specified in standard EN 12.83) with overall hydraulic permeability values of $20 \times 10^{-12}$ to $312 \times 10^{-12}$ m$^3$/s.Pa.m$^2$ (10 to 150 ml/h.mmHg.m$^2$).

In a variation of the invention, to produce the hollow fibre devices of the invention, hollow fibres consisting mainly of polyarylsulphone are selected. Preferably, they contain repeating units with formula (I) or (II) below:

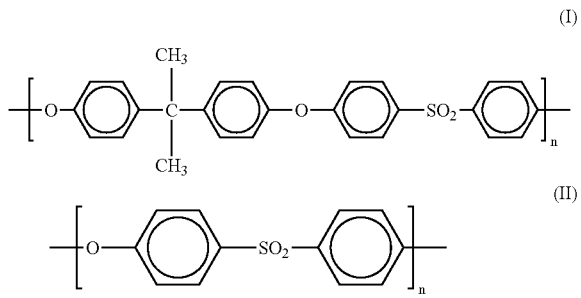

The polyarylsulphone with formula (I), the chain of which contains alkyl radicals, in particular methyl radicals, is termed a polysulphone. The polyarylsulphone with formula (II), which simply contains aryl radicals connected together by an ether or a sulphone group, is termed polyethersulphone.

The invention also pertains to a process for producing a bundle of hollow fibres consisting mainly of polarylsulphone, useful as a semi-permeable membrane in a device for treating blood or plasma by extracorporeal circulation, the process comprising the following steps:

(a) preparing a bundle of hollow fibres with a heterogeneous distribution of fibres within the bundle insofar as the density of the hollow fibres is higher in certain zones of the bundle than in other zones;

(b) mounting the bundle of hollow fibres in a tubular casing comprising two axial openings;

(c) causing a hot, dry gas that is chemically inert towards the hollow fibres, preferably hot, dry air, to circulate through the bundle of hollow fibres, not held at its ends, at a temperature and flow rate that are suitable to cause geometrical heterogeneity of the hollow fibres in the bundle as regards the internal diameter and wall thickness of the hollow fibres;

(d) stopping the hot, dry gas from circulating when the geometrical heterogeneity of the hollow fibres has been obtained.

Adjusting the operating conditions of steps a) and c) affects the characteristics of devices for extracorporeal treatment of blood, in particular the hydraulic permeabilities.

The term "hot, dry gas" as used in the context of the present invention means a hot gas with a relative humidity that does not exceed 10% at the temperature at which the gas is used. Preferably, the temperature of the hot, dry gas at the inlet to the bundle of hollow fibres is 75° C. to 130° C., more preferably 90° C. to 120° C.

Preferably, the flow rate of the hot, dry gas at the inlet to the bundle of hollow fibres is 2 to 5 m$^3$ per hour.

Preferably, the duration of step (c), consisting of circulating a hot, dry gas through the bundle of hollow fibres, is of the order of 1 to 4 hours.

Preferably, circulation of the hot, dry gas is stopped when the temperature of the gas at the outlet from the tubular casing is substantially equal to the temperature of the gas at the inlet to the tubular casing.

The invention also concerns a bundle of hollow fibres resulting from carrying out the production process described above.

Further characteristics and advantages of the invention will become apparent from the detailed description below, concerning variations and embodiments of the present invention.

Reference should also be made to the accompanying drawings, in which.

To provide a detailed illustration of the invention, the production of a particular type of device for extracorporeal treatment of blood in accordance with the present invention will now be described.

1. Production of Hollow Fibre

A polymer solution for extrusion is prepared that contains:

14% by weight of polyarylsulphone, in particular a polyethersulphone (with a weight average molecular weight Mw of 70000 Daltons) miscible with N-methylpyrrolidone (NMP);

5% by weight of a mixture of polyvinylpyrrolidone (PVP) of the K30 and K90 type, miscible with water and NMP;

1% by weight of water;

80% by weight of NMP.

Mixing is carried out at high temperature, of the order of 80-90° C., applying high shear forces. The solution is then cooled, preferably to 20° C.

To obtain a hollow fibre, the above polymer solution is extruded through a die comprising two concentric circular openings, an external annular opening to extrude the polymer solution and an internal central opening for passage of the hollow-fibre centring and precipitating liquid. The external and internal diameters of the annular opening of the die are respectively 500 microns and 350 microns, and the diameter of the internal central opening is 170 microns.

The composition of the hollow-fibre centring and precipitating liquid in this example is a homogeneous mixture of 44% by weight of NMP, 55% by weight of water and 1% by weight of PVP.

Under the conditions of this example, a hollow fibre is formed with an internal diameter of 215 μm and a wall thickness of 50 μm.

The hollow fibre is then carefully washed with water that is free of pyrogenous elements by passing it through a plurality of baths without stretching it.

2. Production of Bundle of Hollow Fibres

In accordance with the invention, when extrusion is complete, after precipitation and washing the hollow fibres, a bundle of hollow fibres is prepared that is substantially rectilinear with a heterogeneous distribution of fibres inside the bundle whereby the density of the hollow fibres is higher at the periphery of the bundle and lower at the centre of the bundle. The chemical nature of the hollow fibres in this example is identical throughout the bundle.

Figure 1:
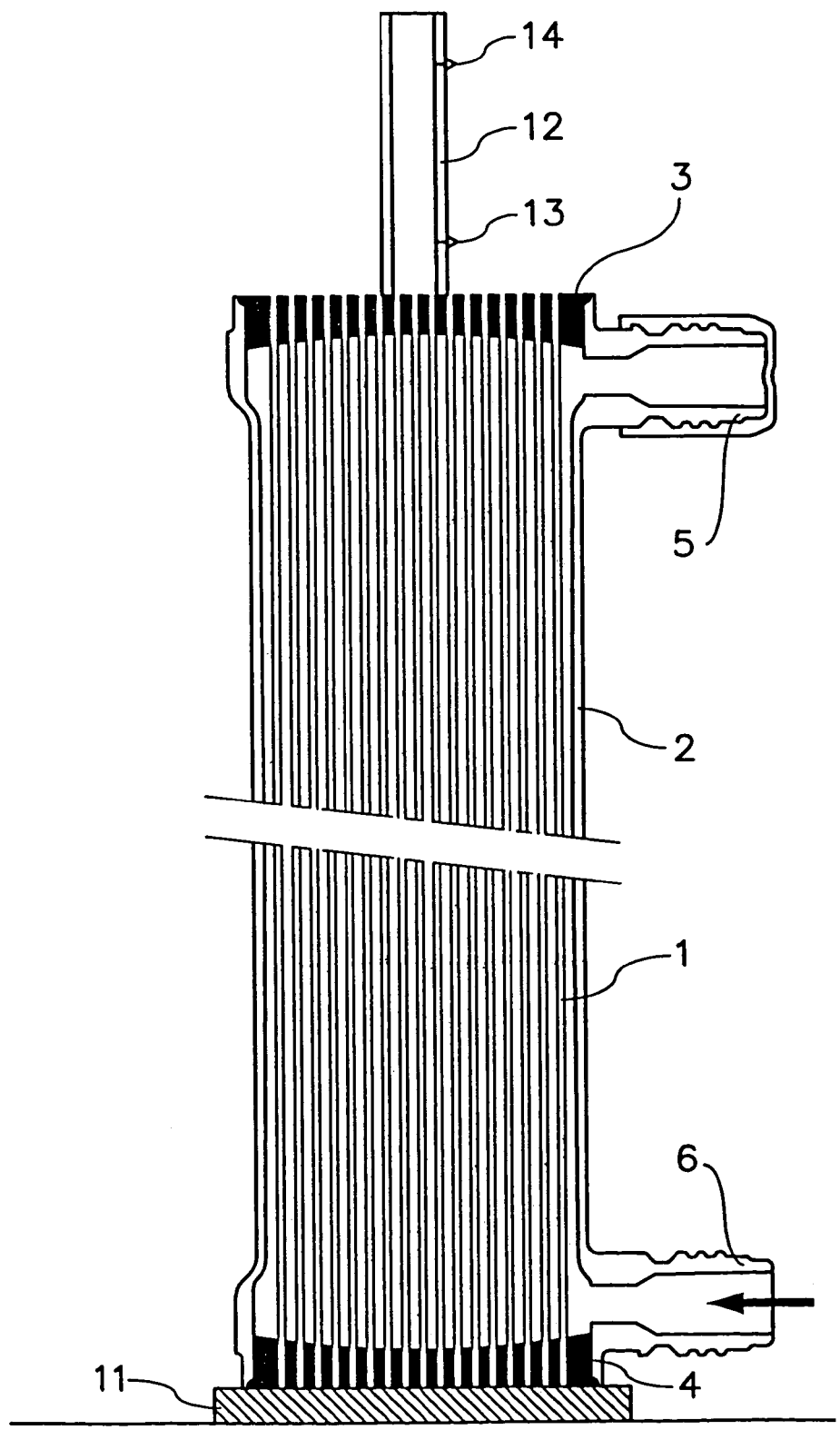
FIG. 1 shows a diagrammatic view in longitudinal section of the device for measuring local hydraulic permeability in accordance with the invention.
Figure 2:
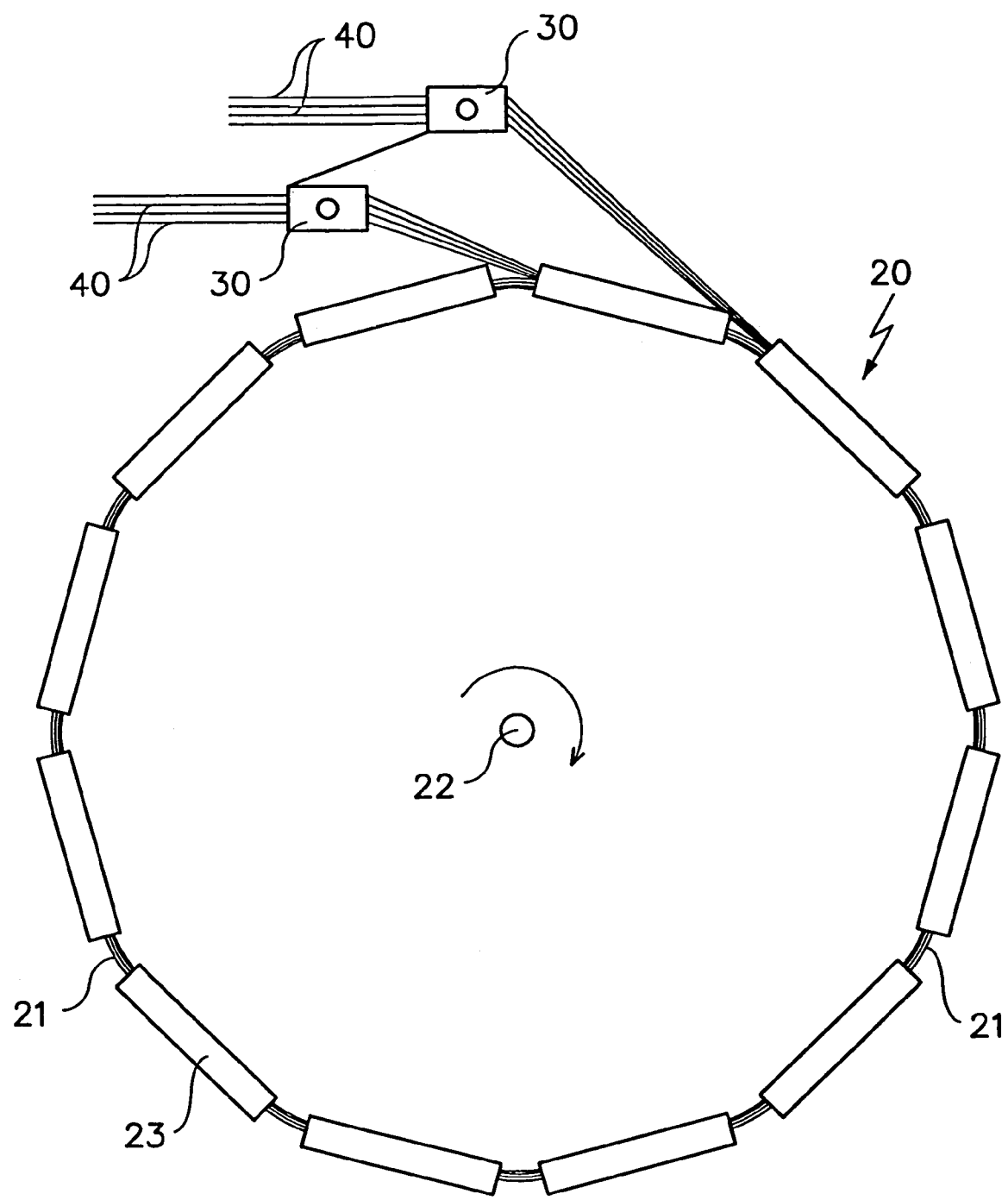
FIG. 2 shows a partial diagrammatic perspective view of a fibre guiding device.
Figure 3:
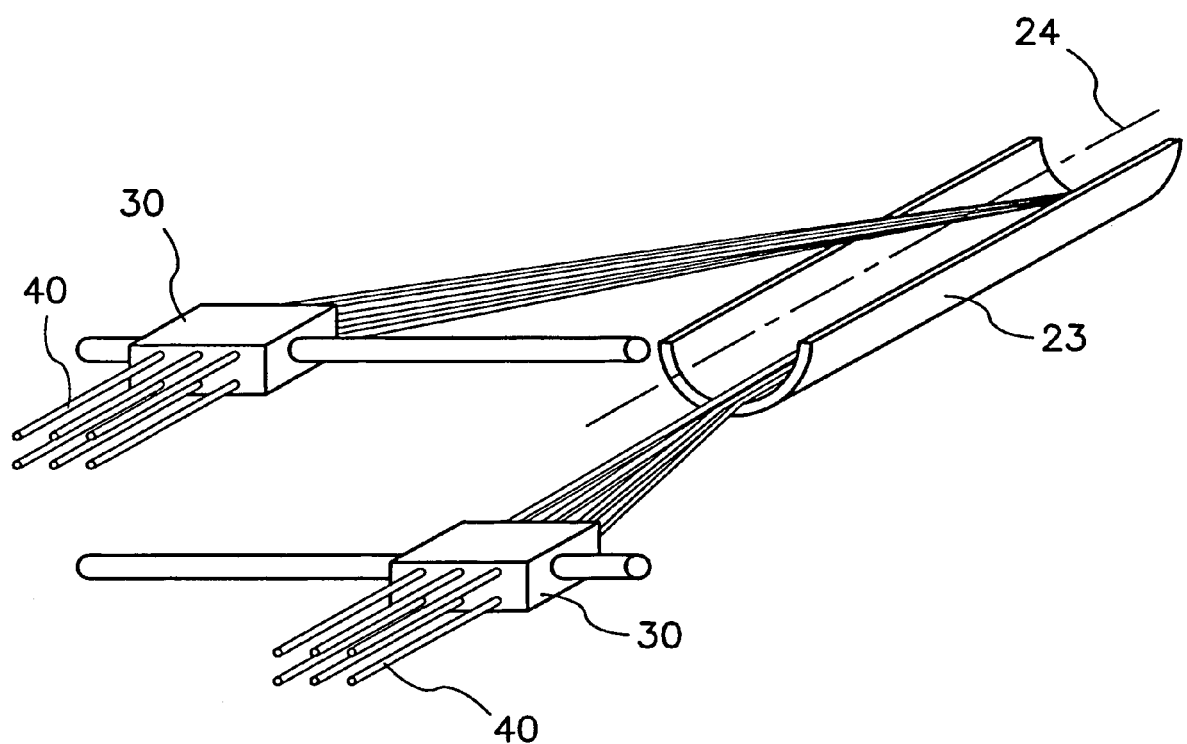
FIG. 3 shows a perspective diagrammatic view of two carriages of the fibre guiding device that guide the hollow fibres into a semi-cylindrical trough.

In this example, preparation of the fibre bundle comprises a fibre guiding step carried out using a fibre guiding device (shown diagrammatically in the accompanying FIGS. 2 and 3). Fibre guiding is an operation that consists of structuring the fibre bundle and results in a criss-crossed arrangement of fibres. To this end, the fibre-guiding device comprises:

- a drum 20 with a winding surface 21 with a regular polygonal cross section that can be rotated about its axis of symmetry 22, each side of the winding surface 21 of drum 20 being provided with a semi-cylindrical trough 23, the axes 24 of the semi-cylindrical troughs 23, which are aligned about the drum 20, being coplanar; and
- at least one carriage 30 (in this case two carriages 30) carrying at least one set of guide rollers (not shown), located a certain distance from the drum 20, to guide and supply at least one hollow fibre 40 (or at least one strand of hollow fibres) to the semi-cylindrical troughs 23, each carriage 30 being movable in a reciprocating motion perpendicular to the plane containing the axes 24 of troughs 23, with a variable amplitude not exceeding the diameter of the semi-cylindrical troughs.

Figure 4:
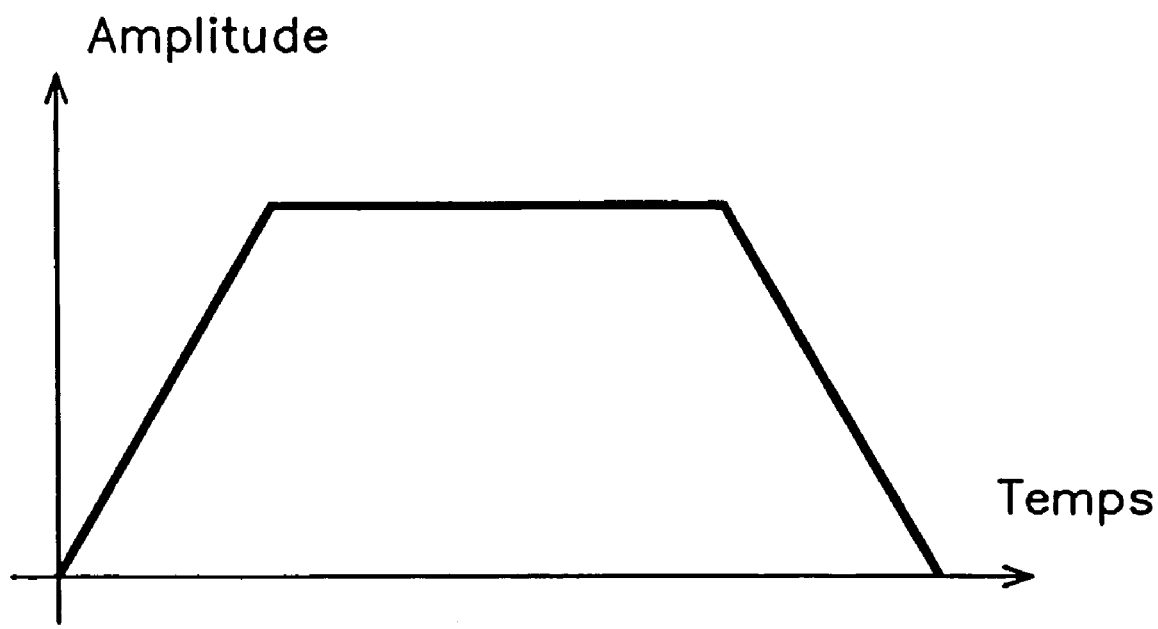
FIG. 4 shows an example of the variation with time of the amplitude of the reciprocating motion of the hollow-fibre guide carriages.

The fibre guiding step consists of winding at least one hollow fibre 40 onto the drum 20, which drum is rotated about its axis of symmetry 22, the hollow fibre being supplied and guided by the guide rollers on at least one carriage 30 to semi-cylindrical troughs 23 turning with the drum 20, to fill the troughs 23. In this example, the reciprocating motion of the two carriages 30 is in phase opposition and the reciprocating motion of each carriage 30 varies with time as shown in FIG. 4 as the troughs 23 are filled, leading to the formation of bundles of hollow fibres:

(1) initially, to fill the bottom of the semi-cylindrical troughs 23, the reciprocating motion amplitude is small;

(2) then the reciprocating motion amplitude varies regularly, increasing to reach a plateau corresponding to a value less than the diameter of the semi-cylindrical troughs 23;

(3) then the reciprocating motion amplitude is kept constant for a certain period; and (4) finally, the reciprocating motion amplitude varies regularly, reducing to a very small value.

Further, during steps (1) to (4) above, the speed of rotation of drum 20 is substantially constant and the speed of displacement of each carriage 30 is substantially constant.

Preferably, the fibres are arranged into a bundle immediately after their production. Between the extrusion device and the fibre-guiding device, they are kept under tension without stretching them. They are wound onto drum 20 at a constant circumferential speed (circumferential speed of drum 20 in rotation about its axis of symmetry 22) in the range 20 to 80 meters/minute. As indicated above, semi-cylindrical troughs 23 corresponding to the number of bundles to be manufactured are fixed to the winding surface 21 of drum 20. In this example, the diameter of the troughs 23 is slightly larger than the diameter of the bundles of hollow fibres before they are subjected to a circulation of hot, dry air, while the length of the troughs is slightly less than that of the bundles of hollow fibres. In this example, the trough diameter is 45 mm with a length of 280 mm. Twelve semi-cylindrical troughs 23 are mounted on the drum 20.

In this example, the hollow fibres leaving the extrusion step are distributed into two groups of fibres using fixed separating rollers (not shown), each group of fibres being separately guided by a set of integral movable rollers carried by each of the respective carriages 30. The two groups of hollow fibres finally meet on the troughs 23 whereupon they are wound around the drum 20. As indicated above, the two carriages 30 are displaced in a reciprocating motion in phase opposition, with a variable amplitude, in this case from 0 to 40 mm. Advantageously, each carriage 30 carries out an odd, non-integer number of movements in one direction per turn of the drum 20 that varies from 3 to 15, preferably 7.1 movements in one direction.

Figure 5:
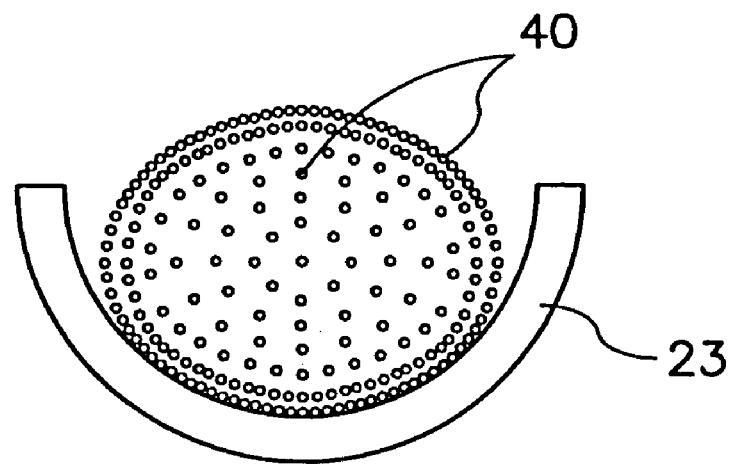
FIG. 5 shows a diagrammatic view in transverse section of a bundle of hollow fibres after a fibre guiding step carried out in the manner described for FIG. 4.
Figure 6A:
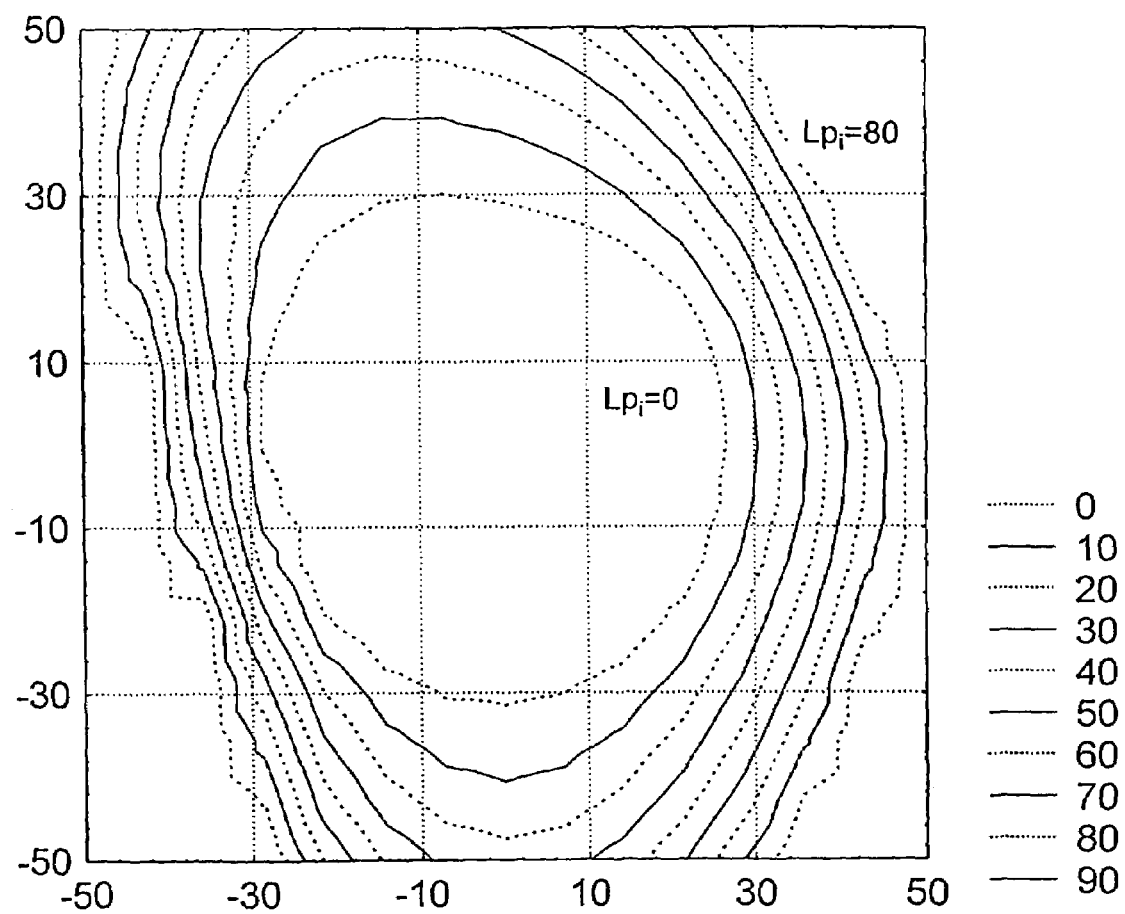
FIGS. 6a, 6b, 6c and 6d show the influence of the conditions of circulation of hot, dry air through the bundle of hollow fibres on the hydraulic permeability of the hollow fibres.
Figure 6B:
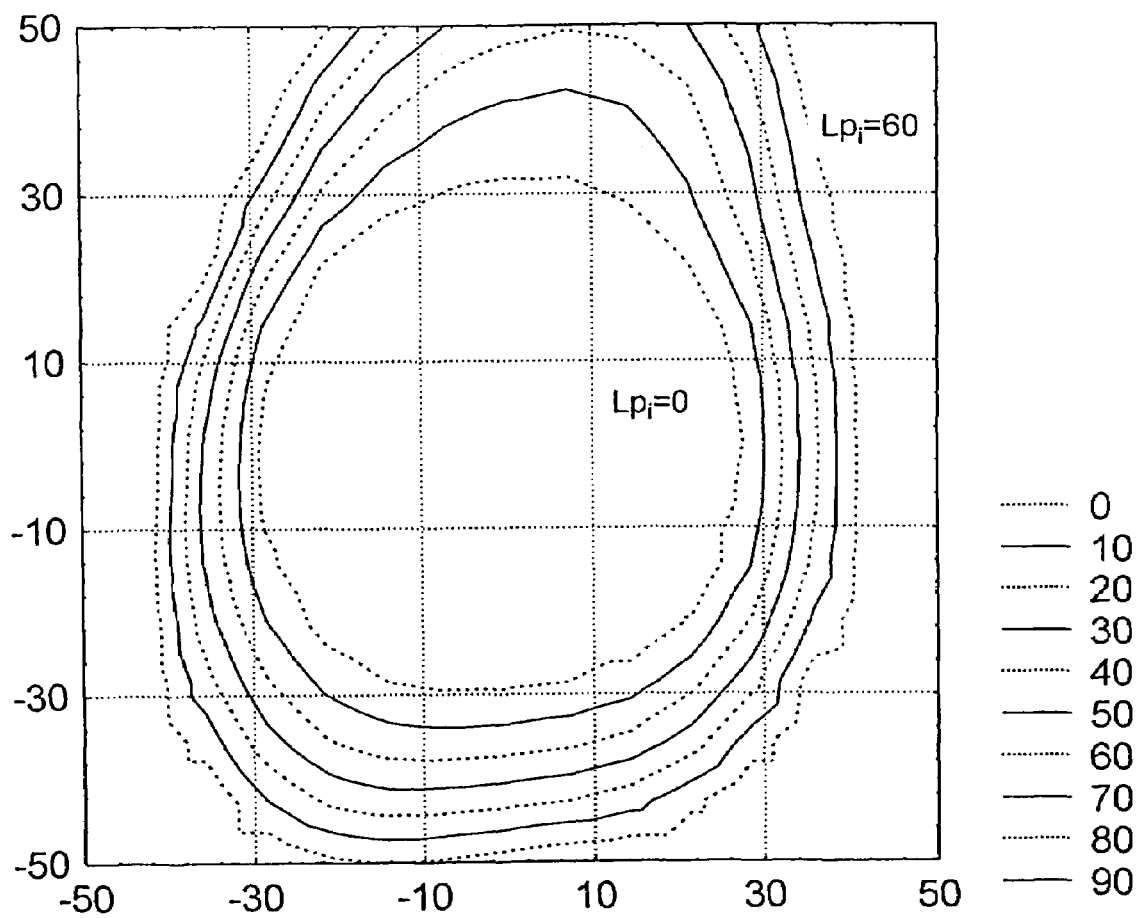
Figure 6C:
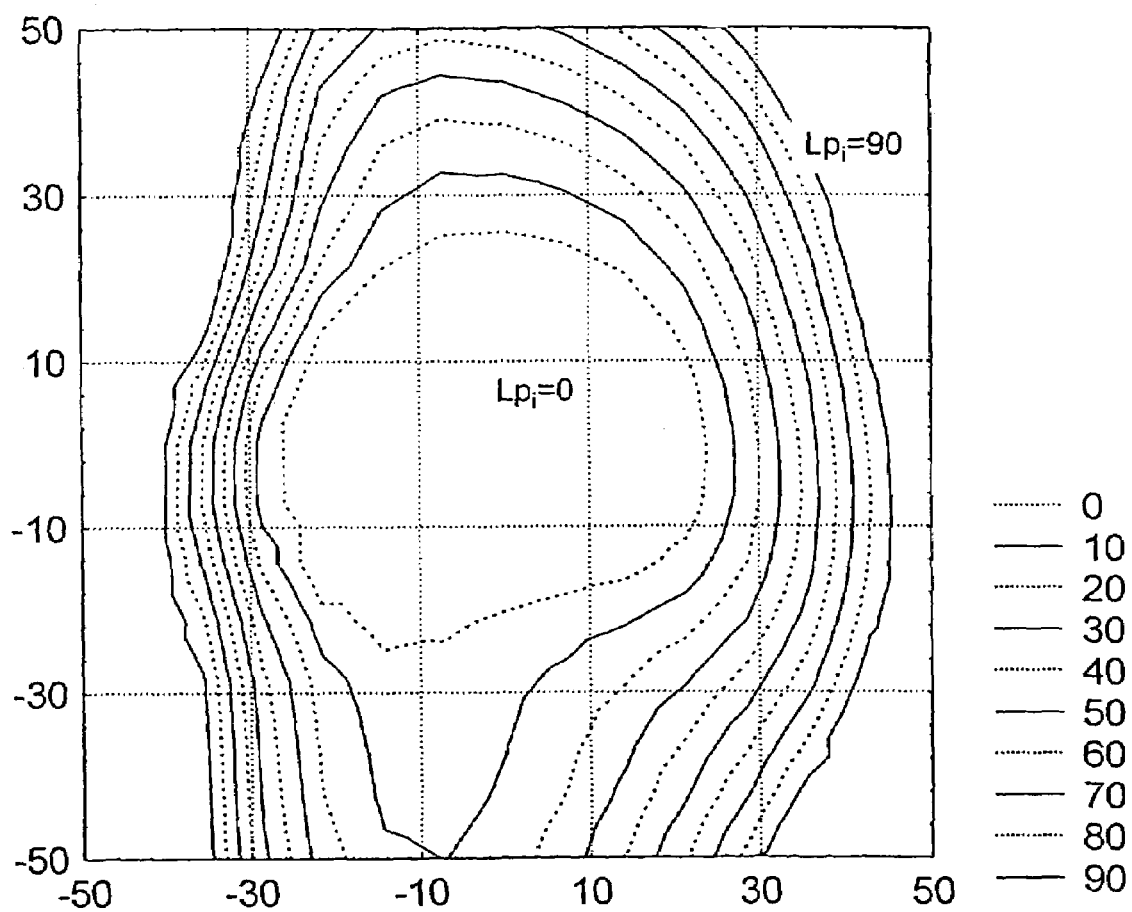
Figure 6D:
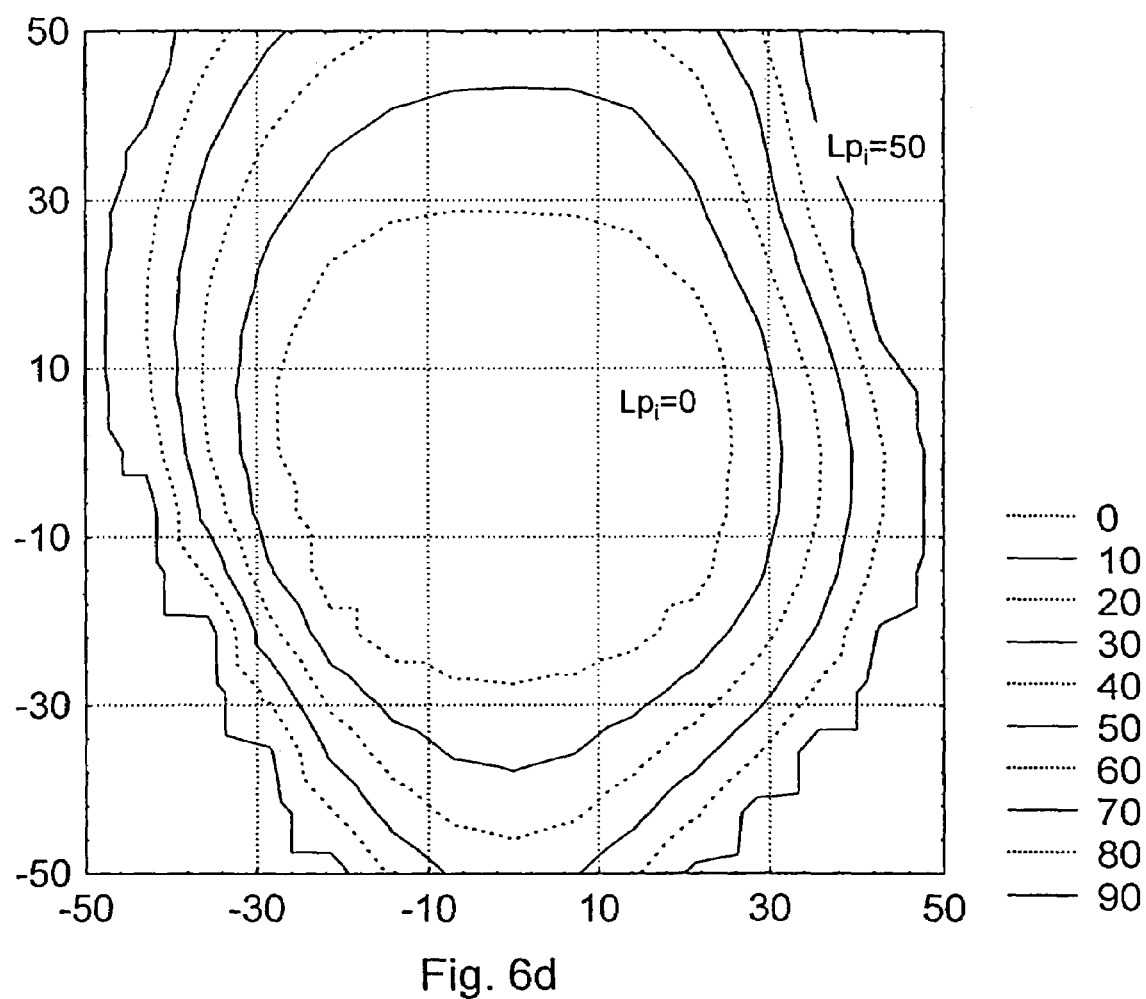

The displacement of the two carriages 30 that guide the fibres 40 towards the troughs 23 with a constant circumferential speed and a variable amplitude influences the structure of the bundle of hollow fibres. The density of the fibres disposed in the trough is inversely proportional to the amplitude of the displacement of the carriages 30: the smaller the displacement amplitude, the higher the density of the fibres placed in the troughs 23. The fibre-guiding step contributes towards heterogeneous distribution of the hollow fibres with a higher fibre density in certain parts of the bundle. In this case, the bundles of hollow fibres, after they have satisfied the conditions regarding the time variation of the amplitude of the reciprocating motion of the guide carriages 30 indicated in FIG. 4, have a higher density at the periphery compared with the density at the centre (see FIG. 5). Further, each bundle comprises two longitudinal peripheral and opposed zones where the densities in hollow fibres are at their highest: these two zones correspond to the start and finish of filling of the troughs 23.

Clearly, the reciprocating motion amplitude of carriages 30 can be varied with time in a different way, and a different distribution of hollow fibres from that described above thus be produced, the zones most dense in hollow fibres then not necessarily being at the periphery of the bundle.

When the predefined number of hollow fibres per trough 23 has been reached, drum 20 is stopped from rotating, troughs 23 are closed with a semi-cylindrical cover (not shown) and the fibres between each trough 23 are cut.

In this example, each bundle of hollow fibres is then transferred into a tubular casing comprising two axial openings and two lateral openings.

After equalising the length of the hollow fibres for each bundle, the operations required to dry the bundles of fibres are carried out. If necessary, firstly, the liquid present in the hollow fibres is eliminated, preferably by centrifuging.

Then, in accordance with the invention, hot, dry air is passed through the bundles of hollow fibres that are not held at their ends, the hot, dry air entering via one axial opening in the casing and leaving via the other axial opening in the casing, the two lateral openings in the casing being closed.

The hot, dry air is circulated under the temperature, flow rate and duration conditions described above, to cause a geometrical heterogeneity of the hollow fibres in the bundle (i.e., differences in the internal diameter and wall thickness of the fibres) and a heterogeneity in the density of the hollow fibres in the bundle.

Advantageously, the hot, dry air is injected via one of the axial openings of the casing with the speed of the circulation front homogeneous over the whole of this opening, under turbulent flux.

The hot, dry air introduced into the casing encounters the zones most dense in hollow fibres (at the periphery of the bundle) and preferentially passes along the less dense zones (in particular at the centre of the bundle). Further, circulating hot air in the casing tends to displace and constrain the hollow fibres towards the periphery of the bundle, against the walls of the casing. This drying step, therefore, also contributes to heterogeneity in the distribution of the hollow fibres in the bundle.

Further, because of the preferential passage of the hot air along the central portion of the bundle, the fibres of the interior of the bundle shrink more (length, internal and external diameters and thickness) than those at the periphery of the bundle.

With such a bundle of hollow fibres, a device can be produced to treat blood or plasma with reduced risks of reverse filtration, an overall hydraulic permeability that can be adjusted to requirements and with transmittances that are higher than those of a conventional device with a similar hydraulic permeability.

Further, with such a bundle, a device can be produced for treating blood or plasma with characteristics (hydraulic permeability, transmittances) that can be independently adjusted to a certain extent so that the hydraulic permeability of the membrane is low flux, medium flux or high flux, while the transmittances, in particular those for toxins and proteins, are maintained at values that are higher than those of a conventional device with a similar hydraulic permeability.

The last steps necessary for finishing the manufacture of a device for treating blood or plasma by extracorporeal circulation in accordance with the invention after stopping the circulation of the hot, dry air as soon as the bundle of hollow fibres is sufficiently dry to allow it to be sealed, are conventional. The principal steps are:
- homogenising the distribution of the fibres, limited to the ends of the bundle;
- sealing, consisting of securing the two ends of the bundle of hollow fibres by adhesion using a seal in which a portion of the length of the fibres is embedded, the ends of the fibres being left open;
- cutting the ends of the bundle;
- closing the tubular casing at its two ends with caps;
- sterilising the medical device.

EXAMPLES 1 TO 5

Dialysers comprising about 8000 hollow polyethersulphone fibres were produced and assembled as in the above detailed description.

Only the conditions for circulating the hot, dry air differed between the examples.

The table below summarises these conditions.

| Example | Air flow rate ($m^3/h$) | Temperature of hot, dry air at inlet into tubular casing, °C. |
|---|---|---|
| Comparative example 1 | 2 | 60 |
| 2 | 2 | 110 |
| 3 | 2 | 120 |

-continued

| Example | Air flow rate ($m^3/h$) | Temperature of hot, dry air at inlet into tubular casing, °C. |
|---|---|---|
| 4 | 4 | 110 |
| 5 | 4 | 120 |

From the results for the measurements of local permeability Lpi, four maps were established by mathematical regression: see FIGS. 6a, 6b, 6c and 6d, which correspond to Examples 2, 3, 4 and 5, respectively. In FIGS. 6a, 6b, 6c and 6d:
- the axes of the abscissas and ordinates, graduated from −50 mm to +50 mm, represent two directions that are perpendicular to each other, of one of the cut surfaces of the ends of the bundle of hollow fibres;
- each curve, closed or otherwise, marked in dotted lines or as a solid line, represents points with the same local hydraulic permeability Lpi, expressed in ml/h.mm-Hg.$m^2$;
- the central curve, shown in dotted lines, represents points with a local hydraulic permeability Lpi of 0 ml/h.mm-Hg.$m^2$;
- the difference between two successive curves is 10 ml/h.mmHg.$m^2$;
- the key given with each figure notes successive values of the local hydraulic permeability Lpi at each curve starting from the central curve.

FIGS. 6a, 6b, 6c and 6d demonstrate that the local hydraulic permeabilities Lpi are higher at the periphery of the bundle than at the centre of the bundle.

The table below also shows the influence of the conditions for circulating hot, dry air on the overall and local hydraulic permeabilities, Lpi, measured before sterilisation.

| | Hydraulic permeability (ml/h · mmHg · $m^2$) | | | |
|---|---|---|---|---|
| Example n° | Overall | Minimum at bundle centre | Maximum at bundle periphery | Max/min ratio |
| 1 (comparative) | 200 | 200 | 200 | 1 |
| 2 | 30 | 1.5 | 80 | 53 |
| 3 | 25 | 0.9 | 63 | 70 |
| 4 | 23 | 4.1 | 98 | 24 |
| 5 | 18 | 1.5 | 46 | 30 |

The table below shows the dimensions of certain hollow fibres before and after circulating hot, dry air through the bundle of Example 2. The fibre dimensions were measured using an optical microscope and the results shown below in the table correspond to an average of measurements over 36 fibres.

| | Internal diameter (μm) | External diameter (μm) | Wall thickness (μm) |
|---|---|---|---|
| Before circulating hot, dry air | 215 | 315 | 50 |
| After circulating hot, dry air: | | | |
| hollow fibres at periphery of bundle | 213.7 | 313.6 | 49.9 |
| hollow fibres at centre of bundle | 205.7 | 299.1 | 46.7 |

EXAMPLES 6 TO 10

Dialysers comprising about 8000 hollow polyethersulphone fibres were produced and assembled as in the above detailed description.

The conditions for producing the dialysers were substantially similar, with the exception of the conditions for circulating the hot, dry air, which differed from one example to another.

The table below shows the conditions and the results of measurements of the overall hydraulic permeability.

| Example n° | Hot air flow rate (m³/h) | Temperature of hot, dry air at inlet (° C.) | Overall hydraulic permeability (ml/h · mmHg · m²) |
|---|---|---|---|
| 6 | ~2, then 1 | 85–90 | 37 |
| 7 | ~4, then 2 | 85–90 | 51 |
| 8 | ~4, then 2 | 75–80 | 54 |
| 9 | ~2 | 90 | 33 |
| 10 | ~1 | 90 | 29 |

EXAMPLES 11 TO 29

Dialysers comprising about 8000 hollow polyethersulphone fibres were produced and assembled as described in the above detailed description.

The conditions for producing the dialysers were substantially similar with the exception of the hot, dry air circulation conditions, which differed between examples.

The table below shows the conditions and the results of measurements of the overall hydraulic permeability Lp and cytochrome C transmittance (Tr), and measurements of the length (L) of the hollow fibres, maximum and minimum, after circulating hot, dry air. The transmittance measurement conditions were: a starting concentration of cytochrome C of 0.05 g/l, a blood flow rate of about 400 ml/min and an ultrafiltration flow rate of about 80 ml/min. The maximum length, Lmax, and the minimum length, L min, corresponded to the length of the longest fibre and shortest fibre in the bundle respectively. The longest fibre was located at the periphery of the bundle, while the shortest was located at the centre of the bundle.

| Example no. | Air flow rate (m³/h) | Temperature of hot, dry air at inlet to tubular casing, ° C. | Lp (ml/h · mm Hg · mm²) | Tr for cytochrome C | Lmax (mm) | L min (mm) | Difference between Lmax and Lmin (mm) |
|---|---|---|---|---|---|---|---|
| 11 | 4.5 | 102 | 46.9 | n.m. | 269.6 | 268.3 | 1.3 |
| 12 | 4.5 | 97.5 | 55.8 | n.m. | 270.4 | 269.4 | 1.0 |
| 13 | 4.0 | 97.5 | 48.7 | n.m. | 270.2 | 269.5 | 0.7 |
| 14 | 4.5 | 100 | 42.6 | 0.23 | 269.8 | 268.9 | 0.9 |
| 15 | 4.5 | 100 | 34.1 | 0.22 | 269.8 | 268.5 | 1.3 |
| 16 | 4.8 | 93 | 58.4 | 0.36 | 270.2 | 269.5 | 0.7 |
| 17 | 4.8 | 93 | 63.3 | 0.39 | 271.0 | 269.5 | 1.5 |
| 18 | 4.8 | 93 | 53.2 | 0.37 | 270.1 | 269.3 | 0.8 |
| 19 | 4.8 | 93 | 47.0 | 0.36 | 270.1 | 269.3 | 0.8 |
| 20 | 4.8 | 93 | 46.7 | 0.34 | 270.3 | 269.4 | 0.9 |
| 21 | 2 | 105 | 45.5 | 0.47 | 270.3 | 267.3 | 3.0 |
| 22 | 2 | 105 | 41.8 | 0.47 | 270.1 | 267.4 | 2.7 |
| 23 | 2 | 105 | 44.5 | 0.47 | 270.6 | 267.2 | 3.4 |
| 24 | 2 | 105 | 35.7 | 0.41 | 270.2 | 267.0 | 3.2 |
| 25 | 4 | 109 | 27.3 | 0.46 | 269.7 | 267.7 | 2.0 |
| 26 | 4 | 109 | 27.2 | 0.52 | 269.1 | 267.1 | 2.0 |
| 27 | 4 | 109 | 24.8 | 0.48 | 269.2 | 267.4 | 1.8 |
| 28 | 4 | 109 | 24.9 | 0.52 | 269.1 | 267.2 | 1.9 |
| 29 | 4.8 | 93 | 68.8 | n.m. | 269.9 | 269.3 | 0.6 | n.m. means: not measured.

Figure 7:
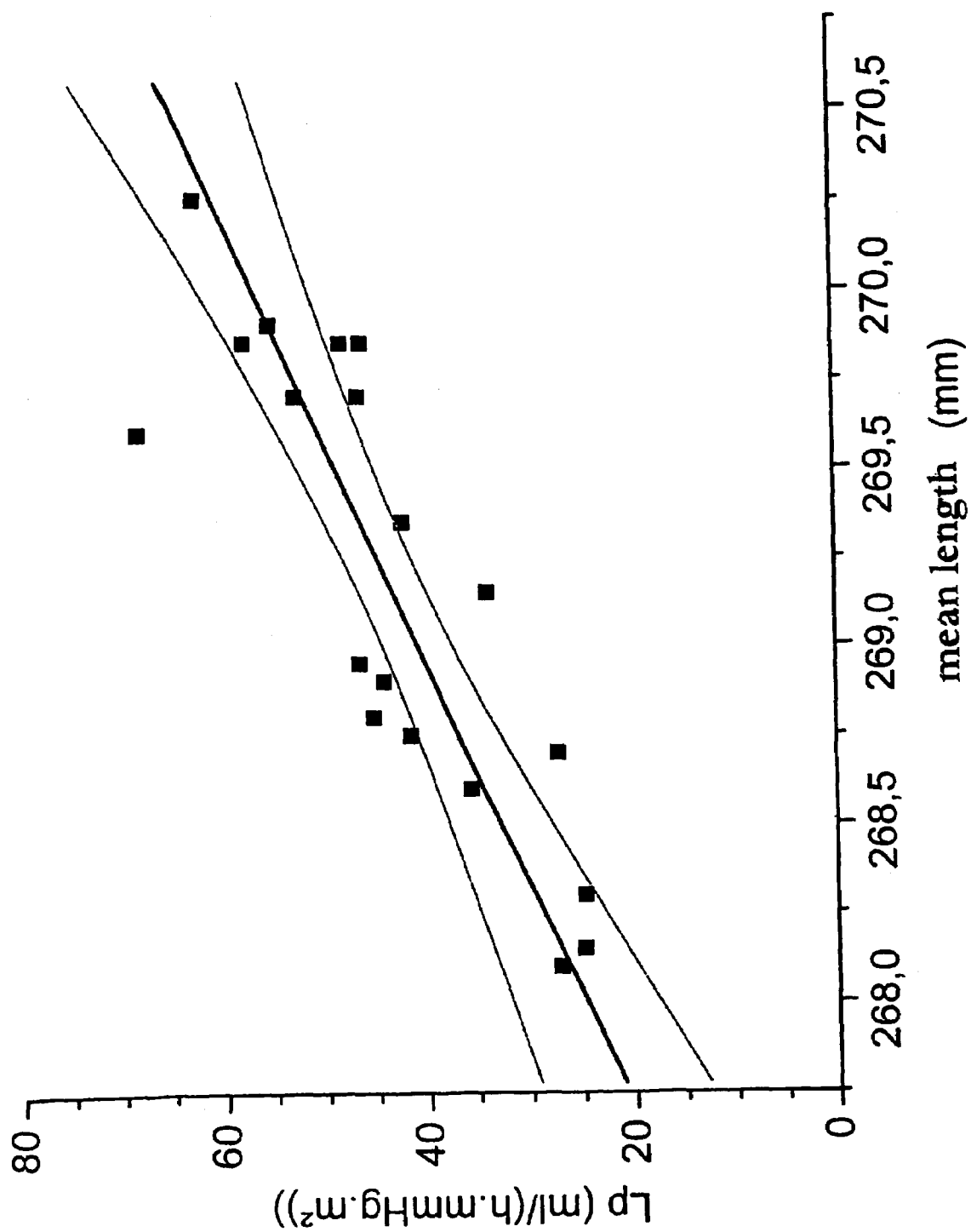
FIG. 7 shows the correlation between the length of the hollow fibre after circulating hot, dry air and its hydraulic permeability.

FIG. 7 illustrates the relationship between the mean fibre length of the bundle after circulating hot, dry air (along the abscissa) and the overall hydraulic permeability, Lp, of the bundle (up the ordinate), established from Examples 11 to 29.

The mean fibre length corresponds to the mean of values Lmax and Lmin given above.

FIG. 7 shows a correlation between this mean fibre length and the overall hydraulic permeability of the bundle.

The invention claimed is:
1. A method for measuring a local hydraulic permeability, Lpi, of a sub-group of hollow fibres of a bundle of hollow fibres mounted in a tubular casing, said casing having first and second ends and a first lateral opening at said first end, the bundle of hollow fibres being fixed in the casing by adhesive seals at said first and second ends, said adhesive seals being cut substantially perpendicular to a longitudinal axis of the bundle of hollow fibres to open a section of the bundle of hollow fibres, said method comprising the steps of:
   sealing the first end of the casing by pressing the casing on a plate to ensure a seal;
   applying a calibrated tube against a portion of the opened section of the bundle of hollow fibres to form a sealed connection between said calibrated tube and said portion of the opened section of the bundle of hollow fibres;
   passing a liquid having a flow rate through the first lateral opening of the casing;
   measuring a time t for the liquid to pass from a first graduation to a second graduation of the tube and calculating the local hydraulic permeability, Lpi, based upon:

$Lpi = V/tPSI$ whereby, V represents a volume of the tube between said first and second graduations;

P represents a transmembrane pressure; and

Si represents the surface area of the hollow fibres belonging to the sub-group to be measured.

2. A method according to claim 1, wherein the casing has a second lateral opening at the second end of the casing, said first end of the casing being beneath the second end of the casing.

3. A method according to claim 1, wherein the calibrated tube and the casing are positioned vertically.

4. A method according to claim 2, comprising a step of setting said adhesive seals on said first and second lateral openings of the casing to form a ready-to-use hollow fibre device for the treatment of blood or plasma by extracorporeal circulation.

5. A method according to claim 4, wherein the step of setting said adhesive seals on said first and second lateral openings of the casing is carried out before said steps of measuring the time t and calculating the local hydraulic permeability, Lpi.

6. A method according to claim 1, wherein liquid is passed through the first lateral opening of the casing at a flow rate of 80 ml/min.

7. A method according to claim 2, wherein the liquid is passed through the first lateral opening while the second lateral opening is closed.

8. A method according to claim 1, wherein the calibrated tube is applied to against a portion of the opened upper cut section of the bundle of hollow fibres against the center of the bundle of hollow fibres to measure a local flow rate at the second end of the casing.

9. A method according to claim 1, wherein the calibrated tube has a diameter of 3.2 cm and a length of about 50 cm.

10. A method according to claim 1, wherein the steps of sealing, applying, passing, and measuring are repeated a plurality of times over remaining portions of the opened section of the bundle of hollow fibres.

11. A method according to claim 9, wherein said local hydraulic permeability measurement is evaluated for a substantially constant number of hollow fibres.

12. A method according to claim 1, further comprising a step of placing the casing containing the bundle of hollow fibres in a vertical position.

* * * * *

UNITED STATES PATENT AND TRADEMARK OFFICE
CERTIFICATE OF CORRECTION

PATENT NO.         : 7,250,108 B2
APPLICATION NO. : 10/874303
DATED               : July 31, 2007
INVENTOR(S)       : Boivin et al.

It is certified that error appears in the above-identified patent and that said Letters Patent is hereby corrected as shown below:

On Title page, item (57), Abstract, line 14, "in which;"
    should read --in which:--;

Col. 12, line 67, "*Lpi=V/tPSI*" should read --*Lpi=V/tPSi*--;

Col. 13, line 13, "selling" should read --setting--.

Signed and Sealed this

Twenty-third Day of October, 2007

JON W. DUDAS
*Director of the United States Patent and Trademark Office*